United States Patent [19]

Gerster

[11] Patent Number: 4,499,270
[45] Date of Patent: Feb. 12, 1985

[54] SUBSTITUTED PYRIDOQUINOXALINE-6-CARBOXYLIC ACIDS AND DERIVATIVES THEREOF

[75] Inventor: John F. Gerster, Woodbury, Minn.

[73] Assignee: Riker Laboratories, Inc., St. Paul, Minn.

[21] Appl. No.: 351,135

[22] Filed: Feb. 22, 1982

Related U.S. Application Data

[62] Division of Ser. No. 254,973, Apr. 16, 1981, Pat. No. 4,348,521.

[51] Int. Cl.³ ............... C07D 471/04; A61K 31/495
[52] U.S. Cl. .................................. 544/344; 544/343; 544/353
[58] Field of Search ......................... 544/344

[56] References Cited

U.S. PATENT DOCUMENTS

| 4,075,206 | 2/1978 | Holmes | 544/344 |
| 4,151,280 | 4/1979 | Rowlands et al. | 544/344 |
| 4,348,521 | 9/1982 | Gerster | 544/344 |

*Primary Examiner*—Glennon H. Hollrah
*Assistant Examiner*—James H. Turnipseed
*Attorney, Agent, or Firm*—Donald M. Sell; James A. Smith; Robert W. Sprague

[57] ABSTRACT

Antimicrobial compounds having the heterocyclic nucleus pyrido[1,2,3-de]quinoxaline are disclosed. The process of making the compounds and novel intermediates are also disclosed.

8 Claims, No Drawings

SUBSTITUTED PYRIDOQUINOXALINE-6-CARBOXYLIC ACIDS AND DERIVATIVES THEREOF

This is a division of application Ser. No. 254,973 filed Apr. 16, 1981 now U.S. Pat. No. 4,348,521.

FIELD OF THE INVENTION

This invention relates to novel compounds having the heterocyclic nucleus known as pyrido[1,2,3-de]quinoxaline. Compounds of the invention have useful pharmacological activity as antimicrobial agents. A process for preparing the compounds and a method of inhibiting the growth of microorganisms using the compounds are also included within the scope of the invention. A further aspect of the invention relates to pharmaceutical compositions containing the compounds.

BACKGROUND ART

Compounds having the simple ring system 1H, 5H-pyrido[1,2,3-de]quinoxaline are reported by Hazelwood, et.al., J. Proc. Roy. Soc. N.S. Wales, 71, 462 (1938); Chem. Abstracts, 33, 610 (1939). A pyrazinophenanthroline derivative is described by Almond and Mann, J. Chem. Soc., 1906 (1951), having the structure:

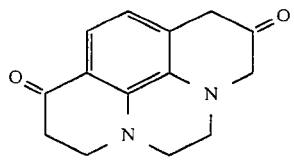

DESCRIPTION OF THE INVENTION

This invention relates to derivatives of 2,3-dihydro-7-oxo-1H,7H, pyrido[1,2,3-de]quinoxaline. The structure and numbering system for this heterocyclic system are shown below:

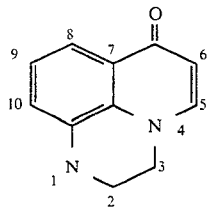

The compounds of the invention may be represented by the following formula:

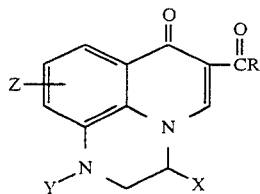

wherein X is hydrogen or methyl; Y is hydrogen, methyl, ethyl, phenyl, or an alkyl chain of three carbon atoms bonded through the terminal carbon to the ten position of the benzo ring to form a compound of the formula:

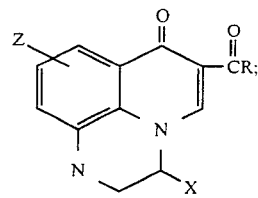

Z is hydrogen, halogen, lower alkyl or lower alkoxy; and R is OH, a lower alkyl ester residue, a lower alkyl amide residue, or —OM wherein M is a pharmaceutically acceptable cation.

The term "lower" is used to refer to alkyl or alkoxy groups having from one to four carbon atoms in straight or branched chain configuration. The term "residue" used in conjunction with the terms "ester" or "amide" refers to the portion of the ester or amide moiety attached to the carbon atom of the carbonyl group.

Compounds of formula I wherein X is methyl have an optically active carbon at the 3-position. All such optical isomers are included within the scope of the invention.

Compounds of formula I wherein R is OH are preferred. However, pharmaceutically acceptable salts of these acids such as alkali metal, alkaline earth, aluminum, iron and other metal and amine salts are generally equivalent in activity to the acids, and in some cases may even offer advantages in absorption, formulation and the like. For example, in agrichemical applications, water-solubility is usually advantageous, and salts of the compounds of the invention are usually employed in formulations for this purpose. Salts of the free acid compounds of the invention are readily prepared by reaction of the acid with a base and evaporation to dryness. The base may be organic, e.g., sodium methoxide or an amine, or inorganic such as sodium hydroxide.

The free acid compounds of the invention are presently preferred for some purposes because of their higher level of anti-microbial activity, particularly when compared to the corresponding esters. The esters are useful for preparation of the corresponding acids, and they, as well as the salts and the amides, are also useful for modifying solubility and persistence of the compounds under conditions of use.

Compounds of formula I where X is methyl are preferred. Compounds wherein Z is chloro or fluoro are preferred, and compounds wherein Y is methyl, phenyl or a three carbon alkyl chain bonded to the ten position of the benzo ring are preferred.

The anti-microbial activity of the compounds of the invention can be demonstrated by the known, standard plate dilution method for bacterial susceptibility to antibiotics. The culture medium employed permits susceptibility testing of fastidious microorganisms towards antibiotics, sulfonamides and other chemotherapeutic agents. Tryptone soy agar (oxoid) of the following composition is the culture medium.

| | |
|---|---|
| Oxoid tryptone | 15 g. |
| Oxoid soy peptone | 5 g. |
| Sodium chloride | 5 g. |
| Oxoid agar-agar No. 3 | 15 g. |

| -continued | |
|---|---|
| Water | 1 liter |

Using this test, the compounds of the invention have been found to have a broad spectrum of activity against gram-positive and gram-negative microorganisms. Activity was demonstrated in both the absence and the presence of 10 percent horse serum.

The standard plate dilution method for bacterial susceptibility provides information on the amount of a compound required to give complete inhibition, partial inhibition or no inhibition of microbial growth on the agar plates. In the tests, the selected compound is added to the agar medium to give concentrations of zero, one, ten and one hundred milligrams per liter. A series of plates with these concentrations is prepared. Ten percent horse serum is added to a second series of such plates. Aliquots of broth culture of each of eleven species of microorganisms are innoculated onto the agar plates containing the various compound concentrations. The plates are incubated at 37° C. in a 10 percent carbon dioxide atmosphere for 18 to 24 hours. The microbial growth on each plate is read visually, and minimal inhibitory concentrations are recorded.

The microorganisms used for this test were:
1. *Staphylococcus aureus*
2. *Bacillus subtilus*
3. *Escherichia coli*
4. *Pseudomonas aeruginosa*
5. *Streptococcus sp.* *
6. *Aspergillus niger*
7. *Candida albicans*
8. *Mima polymorpha*
9. *Herellea vaginicola*
10. *Klebsiella pneumoniae*
11. *Streptococcus fecaelis*

*Strains isolated from dental carries in rats or hamsters at the National Institute of Dental Health and grown in PFY or AIT agar.

All of the compounds of the invention possess antimicrobial activity towards one or more of the above microorganisms.

Many of the compounds of the invention have also shown activity towards anaerobic bacteria, for example Bacteroides sp. and *Clostridium welchii*. Some compounds of the invention have shown useful activity towards *Erwinia amylovora*, a gram-negative microorganism responsible for the plant disease known as fire blight.

It will be understood by those skilled in the art that the species used are representative indicator species, as it would be impractical to screen against all bacteria. It is well known in the art that broad spectrum activity can be predicted on the basis of activity shown against selected representative bacterial species.

Many of the compounds of the invention are active when administered orally to animals. They are excreted in the urine, and are effective urinary tract antibacterials in mammals.

All of the compounds in the invention are active against microorganisms in vitro or topically. In vitro activity is useful in itself, since anti-microbial agents may be used for disinfecting and sterilizing, for example medical and dental equipment, as components of disinfecting solutions. The preferred compounds of the invention are also active in vivo in animals.

The acute oral toxicity of the compounds of the invention generally is moderate to low compared with the effective oral dose, and they have a fair to excellent therapeutic ratio.

Presently preferred compounds of the invention have a broad spectrum of anti-microbial activity and a good therapeutic ratio ($LD_{50}/ED_{50}$). These compounds are: 10-chloro-2,3-dihydro-1,3-dimethyl-7-oxo-1H,7H-pyrido-[1,2,3-de]quinoxaline-6-carboxylic acid; 5,6,8,9-tetrahydro-5-methyl-1(10H)-oxopyrazino[1,2,3,4-1mn][1,10] phenanthroline-2-carboxylic acid; 2,3-dihydro-1,3-dimethyl-9-fluoro-7-oxo-1H,7H-pyrido[1,2,3-de]-quinoxaline-6-carboxylic acid; and 2,3-dihydro-3-methyl-7-oxo-1-phenyl-1H,7H-pyrido[1,2,3-de]quinoxaline-6-carboxylic acid.

The acidic compounds of the invention are ordinarily white or yellowish to green crystalline or amorphous materials when purified. They are substantially insoluble in water, lower alcohols, or hydrocarbons and are more soluble in halogenated solvents, dimethylformamide and the like. The esters and amides are generally somewhat more soluble in organic solvents. The alkali metal salts have appreciable solubility in water and lower alcohols.

The compounds of the invention may be formulated by incorporating them into conventional pharmaceutical carrier materials, either organic or inorganic, which are suitable for oral or intraperitioneal application. For in vitro or topical use, simple aqueous solutions or suspensions are most conveniently employed. For this purpose, concentrations of the order of 100 parts per million up to about 5 parts per thousand are suitable, and the formulation is used by immersing objects to be treated therein, or by local application to an infected area.

The amount of compound to be used, for example, for oral treatment of a microbial urinary infection, will be an effective amount less than a toxic amount. The amount to be administered to control an infection will depend on the species, sex, weight, physical condition and many other factors. Usually the amount will be less than 100 mg./kg. per dose. Conveniently this is administered in the form of the usual pharmaceutical preparations such as capsules, tablets, emulsions, solutions and the like. Excipients, fillers, coatings, etc., are employed with tablets or capsules, as is well known in the art.

It is known to the art that anti-microbial agents are used as growth promoters in various animal and bird species. Although not yet verified, it is inferred from the outstanding anti-microbial activity of the compounds of the invention that they can be used for this purpose also. Compounds of the invention may also be used for the control of microbial (e.g., *Erwinia amylovora*) infections of plants, e.g., by spraying or dusting formulations of these compounds onto the affected area.

The compounds of the invention are prepared starting with 1,2,3,4-tetrahydroquinoxaline or a 1,2,3,4-tetrahydroquinoxaline derivative of the formula:

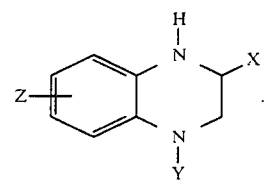

II wherein X, Y and Z are as defined above for formula I.

Many compounds of formula II are known, or they may be readily prepared using known procedures from known starting materials. Some compounds of formula II, such as substituted 1-phenyl-1,2,3,4-tetrahydroquinoxalines of the formula:

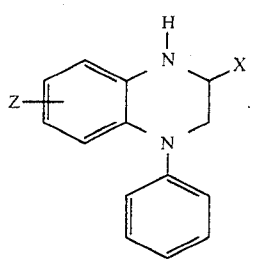

III wherein X and Z are as defined above, are novel and are prepared from known and/or readily prepared starting materials. 2-oxo-1-phenylquinoxaline and substituted derivatives thereof are known intermediates useful in the preparation of compounds of formula III. The oxo group has been found to be readily reduced, e.g., with diborane, to provide the desired 1-phenyl-1,2,3,4-tetrahydroquinoxaline intermediates.

In order to prepare the final product compounds of the invention, diethyl ethoxymethylenemalonate is condensed with an optionally-substituted 1,2,3,4-tetrahydroquinoxaline by heating without solvent at 100° to 200° C. for about one to five hours. The novel intermediates obtained are compounds of the formula:

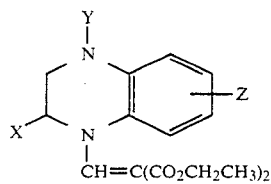

IV wherein X, Y and Z are as defined above for formula I. These novel intermediates are generally oils which need not be isolated or purified. Instead, polyphosphoric acid is added, and the solution is heated at 100° to 140° C. to effect a condensation to provide esters of the acids of formula I. The final step, if the acid compound is desired, is saponification of the esters. Other esters and amides, as well as salts, can be prepared by known methods, e.g., for salts, simple neutralization of an acid with an equivalent of base in an organic solvent followed by evaporation. Amides of the acids of the invention are prepared by conventional techniques, such as by reacting the corresponding acid of formula I with e.g., thionyl chloride, then reacting the acid chloride with ammonia or an amine to provide the amide.

The following examples are provided to illustrate the synthetic methods useful to obtain compounds of the invention, and are not intended to be limiting of the invention.

EXAMPLE 1

Step A

A mixture of 0.0765 mole (15 g) of 8-chloro-1,3-dimethyl-1,2,3,4-tetrahydroquinoxaline and 0.0765 mole (16.5 g) of diethyl ethoxymethylenemalonate is heated under a nitrogen atmosphere at 145° to 150° C. for about 75 minutes. The solution is cooled, 70 g of polyphosphoric acid are added and the mixture is heated under nitrogen at 110° to 120° C. for 45 minutes. The hot solution is poured into water with stirring and a white solid precipitates. The product is recrystallized from ethanol to provide ethyl 10-chloro-2,3-dihydro-1,3-dimethyl-7-oxo-1H,7H-pyrido[1,2,3-de]quinoxaline-6-carboxylate, m.p. 259°–261° C. Analyis: Calculated for $C_{16}H_{17}ClN_2O_3$: %C, 60.0, %H, 5.35; %H, 8.75; Found: %C, 60.0; %H, 5.3; %N, 8.9.

Step B

A mixture of 13.8 g of ethyl 10-chloro-2,3-dihydro-1,3-dimethyl-7-oxo-1H, 7H-pyrido[1,2,3-de]quinoxaline-6-carboxylate and 600 ml of three percent sodium hydroxide solution is heated on a steam bath for five hours. The solution is treated with decolorizing charcoal, filtered and neutralized to pH 7 with acetic acid. The product is separated by filtration, washed with water and recrystallized from N,N-dimethylformamide to provide yellow crystals of 10-chloro-2,3-dihydro-1,3-dimethyl-7-oxo-1H,7H-pyrido[1,2,3-de]quinoxaline-6-carboxylic acid, m.p. 243°–245° C. Analysis: Calculated for $C_{14}H_{13}ClN_2O_3$: %C, 57.5; %H, 4.5; %N, 9.6. Found %C, 58.0; %H, 4.3; %N, 9.7.

Using the methods of Example 1 and starting with diethyl ethoxymethylenemalonate and various heterocyclic starting materials, additional compounds of the invention are prepared as shown in the following Table I:

TABLE I

| Starting Material | Product | Melting Point |
|---|---|---|
| (structure) | (structure) | 223.5–225 |

TABLE I-continued
| Starting Material | Product | Melting Point |
|---|---|---|
| 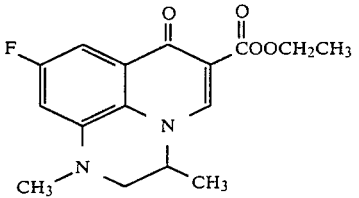 | 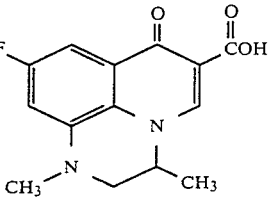 | 274–277 |
| 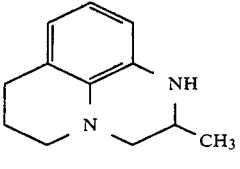 | 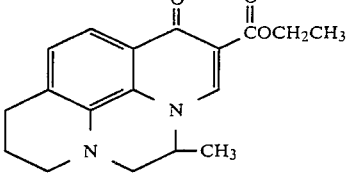 | 178–180 |
| 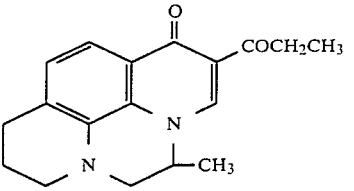 | 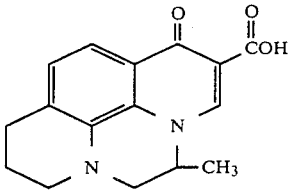 | 289–291 |
| 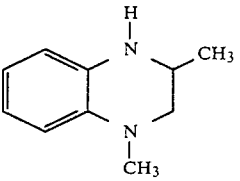 | 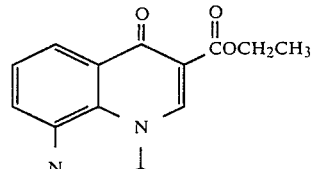 | |
| 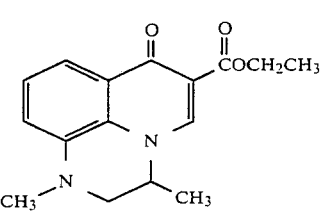 | 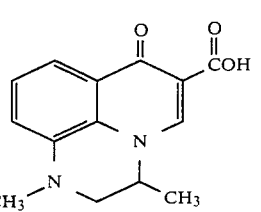 | 269–271 |
| 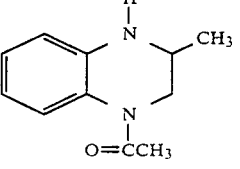 | 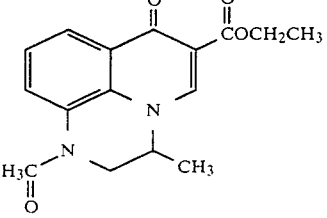 | |
| 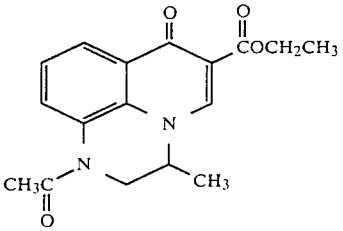 | 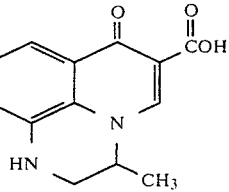 | >250 |

TABLE I-continued

| Starting Material | Product | Melting Point |
|---|---|---|
| [1-acetyl-1,2,3,4-tetrahydroquinoxaline] | [8-(N-acetyl-N-(2-aminoethyl))-3-propanoyl-4-oxoquinoline] | |
| [8-(N-acetyl-N-(2-aminoethyl))-3-propanoyl-4-oxoquinoline] | [8-(2-aminoethylamino)-4-oxoquinoline-3-carboxylic acid] | >300 (dec.) |
| [3-methyl-1-phenyl-1,2,3,4-tetrahydroquinoxaline] | [8-(N-phenyl-N-(2-propyl))-3-propanoyl-4-oxoquinoline] | |
| [8-(N-phenyl-N-(2-propyl))-3-propanoyl-4-oxoquinoline] | [8-(N-phenyl-N-(2-propyl))-4-oxoquinoline-3-carboxylic acid] | 268–270 |

EXAMPLE 14

A mixture of 0.0894 mole (1.7 g) of optically purified (+) 1-acetyl-3-methyl-1,2,3,4-tetrahydroquinoxaline and 0.009 mole (1.9 g) diethyl ethoxymethylenemalonate is heated over one hour to 200° C. and maintained at that temperature for 1.5 hours. After cooling, .5 g of polyphosphoric acid are added and the mixture is heated at 120° C. until foaming stops. The mixture is stirred into water and the solution is made strongly basic with 25 percent sodium hydroxide. The solution is stirred and heated on a steam bath for one hour, then neutralized with acetic acid. Cooling, followed by filtration provides an olive green solid R(+) 2,3-dihydro-3-methyl-7-oxopyrido[1,2,3-de]quinoxaline-6-carboxylic acid, m.p.>250° C. Analysis: Calculated for $C_{13}H_{12}N_2O_3$: %C, 63.9; %H, 5.0; %N, 11.5; Found: %C, 63.4; %H, 5.0; %N, 11.6. Optical rotation $[\alpha]_{21}^D = 93 \pm 3 + (C=0.594,$ N,N-dimethylformamide: ethanol, 1/1).

EXAMPLE 15

A solution of 0.186 mole (25 g) of 1,2,3,4-tetrahydroquinoxaline is dissolved in 250 ml of ethanol and 17.6 ml of acetic anhydride is added dropwise with stirring. The solution is then diluted with 750 ml of water and basified with 1N sodium hydroxide. The solution is extracted with chloroform, the organic extracts are dried and then evaporated to provide the solid product, 1-acetyl-1,2,3,4-tetrahydroquinoxaline.

EXAMPLE 16

Using the method of Example 15, 3-methyl-1,2,3,4-tetrahydroquinoxaline is reacted with acetic anhydride to provide 1-acetyl-3-methyl-1,2,3,4-tetrahydroquinoxaline.

EXAMPLE 17

To a stirred solution of 0.2 mole (34.8 g) of 1,3-dimethyl-2-oxoquinoxaline in 300 ml of dry tetrahydrofuran is added dropwise 0.24 mole (240 ml of 1 M) diborane in tetrahydrofuran. The solution is stirred one additional hour, then heated at its reflux temperature for one day. After cooling, about 40 ml of water is added, followed by 2 equivalents of 4N hydrochloric acid. The solution is heated at reflux for one hour, then evaporated to provide a solid residue. The residue is dissolved in water. The solution is basified and then extracted with diethyl ether. The ether is dried, then evaporated to provide an oil. Distillation provides 1,3-dimethyl-1,2,3,4-tetrahydroquinoxaline, b.p. 85° C/0.1 mm of Hg. Analysis: Calculated for $C_{10}H_{14}N_2$: %C, 74.0; %H, 8.7; %N, 17.4; Found: %C, 74.2; %H, 8.9; %N, 17.3.

EXAMPLE 18

Using the method of Example 17, 3-methyl-2-oxo-1-phenyl-quinoxaline is reduced to produce 3-methyl-1-phenyl-1,2,3,4-tetrahydroquinoxaline, m.p. 91°–93° C. Analysis: Calculated for $C_{15}H_{16}N_2$: %C, 80.3; %H, 7.2; %N, 12.5; Found: %C, 80.3; %H, 7.1; %N, 12.6.

The following acid compounds of the invention are prepared using the method of Example 1 and starting with diethyl ethoxymethylenemalonate and the heterocyclic starting materials shown:

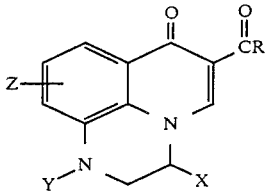

What is claimed is:

1. A compound of the formula wherein X is hydrogen or methyl; Y is hydrogen, methyl, ethyl or phenyl ; Z is hydrogen, halogen, lower alkyl or lower alkoxy; and R is OH, a lower alkyl ester residue, a lower alkyl amide residue, or OM wherein M is a pharmaceutically-accepted cation.

2. A compound according to claim 1 wherein R is OH.

3. A compound according to claim 1 wherein X is methyl.

4. A compound according to claim 1 wherein Z is halogen.

5. A compound according to claim 3 wherein Z is halogen.

6. The compound 10-chloro-2,3-dihydro-1,3-dimethyl-7-oxo-1H,7H-pyrido[1,2,3-de]quinoxaline-6-carboxylic acid according to claim 2.

7. The compound 2,3-dihydro-1,3-dimethyl-9-fluoro-7-oxo-1H,7H-pyrido[1,2,3-de]quinoxaline-6-carboxylic acid according to claim 2.

8. The compound 2,3-dihydro-3-methyl-7-oxo-1-phenyl-1H,7H-pyrido [1,2,3-de]quinoxaline-6-carboxylic acid according to claim 2.

* * * * *